United States Patent
Bonin et al.

(10) Patent No.: US 8,958,058 B2
(45) Date of Patent: Feb. 17, 2015

(54) APPARATUS, PROCESS, AND SYSTEM FOR MONITORING THE INTEGRITY OF CONTAINERS

(75) Inventors: Michel Pierre Bonin, Danville, CA (US); Thomas Lawrence Harvill, Alamo, CA (US); Jared Hubert Hoog, Fairfield, CA (US)

(73) Assignee: Process Metrix, Pleasanton, CA (US)

( * ) Notice: Subject to any disclaimer, the term of this patent is extended or adjusted under 35 U.S.C. 154(b) by 584 days.

(21) Appl. No.: 13/296,301

(22) Filed: Nov. 15, 2011

(65) Prior Publication Data

US 2013/0120738 A1    May 16, 2013

(51) Int. Cl.
| | |
|---|---|
| *G01N 25/72* | (2006.01) |
| *G01S 17/88* | (2006.01) |
| *G01B 11/06* | (2006.01) |
| *G01S 17/02* | (2006.01) |
| *F27D 21/00* | (2006.01) |

(52) U.S. Cl.
CPC ............... *G01S 17/88* (2013.01); *G01N 25/72* (2013.01); *G01B 11/06* (2013.01); *G01S 17/023* (2013.01); *F27D 2021/0085* (2013.01)
USPC .......................................................... 356/73

(58) Field of Classification Search
USPC ................... 356/72–73; 374/4, 137, 141–142
See application file for complete search history.

(56) References Cited

U.S. PATENT DOCUMENTS

| | | | | |
|---|---|---|---|---|
| 4,893,933 | A | * | 1/1990 | Neiheisel et al. .............. 356/608 |
| 5,127,736 | A | * | 7/1992 | Neiheisel ....................... 356/602 |
| 6,188,079 | B1 | | 2/2001 | Juvinall et al. |
| 6,198,102 | B1 | | 3/2001 | Shepherd |
| 7,758,239 | B2 | * | 7/2010 | Ignatowicz .................... 374/139 |
| 7,924,438 | B2 | | 4/2011 | Kleinloh et al. |
| 2006/0192123 | A1 | | 8/2006 | Hamelin et al. |

FOREIGN PATENT DOCUMENTS

JP    09072852 A    3/1997

OTHER PUBLICATIONS

International Search Report issued on May 15, 2013 on the related International Application of No. PCT/US2012/064727 filed on Nov. 12, 2012.

\* cited by examiner

*Primary Examiner* — Kara E Geisel
(74) *Attorney, Agent, or Firm* — Mardson Q. McQuay

(57) ABSTRACT

Apparatuses, systems, and methods to monitor the integrity of a container protected by a refractory material are disclosed having a first radiation detector to measure an external surface temperature of the container, a first radiation source to measure a thickness of the refractory material, and a central controller configured to display to a user the measurement of the external surface temperature of the container and the measurement of the thickness of the refractory material.

20 Claims, 7 Drawing Sheets

APPARATUS, PROCESS, AND SYSTEM FOR MONITORING THE INTEGRITY OF CONTAINERS

BACKGROUND

1. Technical Field

Embodiments of the subject matter disclosed herein relate generally to apparatuses, methods and systems and, more particularly, to mechanisms and techniques for monitoring vessels or containers configured to hold materials having an elevated temperature.

2. Discussion of the Background

Metallic vessels or containers of various sizes and shapes designed to hold materials at elevated temperatures are widely used in many industrial applications. Example of these applications include, but are not limited to, gasification processes in chemical and power production, Electric-Arc Furnaces (EAF), Basic Oxygen Furnaces (BOF), ladles, blast furnaces, degassers, and Argon-Oxygen-Decarburization (AOD) furnaces in steel manufacturing. As known in the art, these containers are normally lined with refractory material installed, in brick form or cast in monolithic blocks in order to protect the metallic part of the vessel from the high-temperature contents placed therein; however, due to normal wear and tear of the refractory material through the combined effects of oxidation, corrosion and mechanical abrasion, some portion of the refractory surface in contact with the molten metal is lost during processing, thus requiring frequent inspection so as to assure extended use by performing early localized repair in order to avoid catastrophic failures and unnecessary or premature refurbishment of the entire vessel's refractory lining.

Before the advance of optically based inspection techniques, inspection of ceramic linings to detect unacceptable levels of lining thickness was performed visually by an experienced operator looking for dark spots in the lining indicating either high localized heat transfer rates to the refractory material and metallic shell or possible excessive wear and the need for lining repair. Such an approach introduces a combination of art and science, exposes the container operator to unnecessary industrial hazards, reduces the frequency of inspections, and lacks the desired accuracy. In addition, costs associated with the installation and repair of ceramic linings have increased significantly over the past twenty years as refractory materials have been reformulated for application-specific installations. In order to improve the efficient use of these more expensive refractory materials, several conventional techniques have been developed to minimize the above-summarized risks including those configured to measure directly the wear on the refractory material and those adapted to measure the effect of the refractory wear on the metallic vessel, such as for example, the indirect monitoring of heat transfer rates to the vessel. However, as summarized below, these conventional techniques have several limitations.

As to conventional techniques configured to measure quantitative refractory wear directly by use of a laser, for example, because the diameters of the lasers are of finite sizes (e.g., approximately 40 to 60 mm in some applications), potential refractory defects with characteristic dimensions smaller than the laser beam diameter, such as a small hole in the lining, are very difficult, if not impossible, to detect, making the localized piece of missing brick also difficult to detect. Moreover, because of the high angle of incidence between the laser beam and the ladle walls, the size of the hole, when one is detected, appears to the operator or laser scanner to be smaller than it actually is.

In addition, localized slag buildup on interior ladle surfaces may make it difficult to detect areas were lining repairs may be needed. That is, as steel is drained from the ladle, the small amount of slag carried over from converter tapping or introduced at the ladle metallurgy furnace can form a coating on the walls or bottom of the ladle. Because much of the accreted slag dissolves into the next ladle heating cycle, comparison of heat-to-heat measurements can sometimes reveal slag accumulation in a prior measurement. However, for any single heat, techniques that use lasers are not capable of resolving the difference between remaining refractory and slag build-up on the interior ladle surfaces. As such, in the presence of slag accumulation, the system will over-predict the lining thickness or under predict the amount of lost refractory—both undesirable limitations in practice.

Finally, another potential problem that may not be detected by laser-based system is the result of finning, which occurs when molten steel naturally enters small gaps (e.g., small openings with a characteristic dimension of approximately 1-5 mm) that develop between the bricks in a refractory-lined vessel. As understood by those of ordinary skill in the arts, finning has the potential to eventually form a metal bridge between the molten metal contained in the ladle and the solid metallic outer shell. Minor finning only causes localized heating of the ladle shell. However, with time, minor finning may become severe and result in melting of the ladle shell and subsequently leakage of molten steel. Thus, while conventional contouring systems are a useful tool to characterize the interior profile of the vessel, there are situations in which the apparent thickness measurement alone may not be sufficient to prevent breakouts.

Examples of conventional techniques configured to measure the qualitative effect of refractory wear on the metallic vessel are those adapted to estimate the temperature on the outside surfaces of the vessel. As the internal refractory material wears and becomes thin, the temperatures of the metal shell in the compromised areas increase due to the increased heat transfer from the molten materials to the vessel. Such measurements are typically done with the ladle hanging from a crane, shortly after the ladle leaves a slab caster, and are used primarily to determine when the container should be removed from service. This qualitative measurement gives an indication of hot spots on the ladle shell independent of the cause (i.e., impending failures due to thinning of the lining, or finning, or both) and, as such, are a direct measure of the nominal health of the "containment." However, those of ordinary skill in the applicable arts will understand that these techniques only provide qualitative information and are not capable of providing detailed information characterizing the wear rate of the lining itself. The local thickness of the refractory lining, the possible existence of finning effects, the time that the molten metal was contained in the ladle, the temperature history of the molten material while it was in the ladle, the processing history (i.e. via ladle metallurgy furnaces) of the molten material while in the ladle, and the radiative properties of the ladles' exterior surface all contribute to the apparent temperature of the metal shell. Thus, the external temperature measurements are only useful on a relative basis, and the lack of quantitative information in the data precludes determination of wear rates and refractory optimization in the ladle.

Therefore, based at least on the above-noted challenges of conventional techniques, what is needed are devices, systems, and methods that will minimize or eliminate inconsistencies in the measured data of refractory lining and external surface temperature of metallic vessels configured to carry materials at temperatures above the melting point of the metal. This will allow the early detection and inspection for molten metal creep or small holes in the lining—all of which can contribute to lining, failure, thereby increasing operational safety while reducing operating costs associated with expensive cleanup operations and potential production down time.

SUMMARY

According to one exemplary embodiment, an apparatus configured to monitor the integrity of a container protected by a refractory material is disclosed that includes a first radiation detector configured to measure an external surface temperature of the container; a first radiation source configured to measure a thickness of the refractory material; and a central controller configured to display to a user the measurement of the external surface temperature of the container and the measurement of the thickness of the refractory material.

According to one exemplary embodiment, a system to monitor the integrity of a container protected by a refractory material is disclosed that includes a thermographic device configured to measure an external surface temperature of the container; a refractory thickness measuring device configured to measure a thickness of the refractory material; and a central controller configured to display to a user the measurement of the external surface temperature of the container and the measurement of the thickness of the refractory material.

According to one exemplary embodiment, a method for monitoring the integrity of a container having an internal layer of a refractory material is disclosed that includes the steps of providing a first radiation detector configured to measure an external, surface temperature of container; providing a first radiation source configured to measure a thickness of the refractory material; and providing a central controller configured to display to a user the measurement of the external surface temperature of the container and the measurement of the thickness of the refractory material.

BRIEF DESCRIPTION OF THE DRAWINGS

The accompanying drawings (not drawn to scale), which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of apparatuses, systems, or methods capable of detecting potential failure locations in a container having a lining material to protect the same against elevated temperatures in a steel making application. However, the embodiments to be discussed next are not limited to these sets, but may be applied to other containers having a liner material exposed to an elevated temperature as compared to the melting point of the material of which the container is made, whose liner integrity needs to be determined in order to avoid unexpected failures.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1:
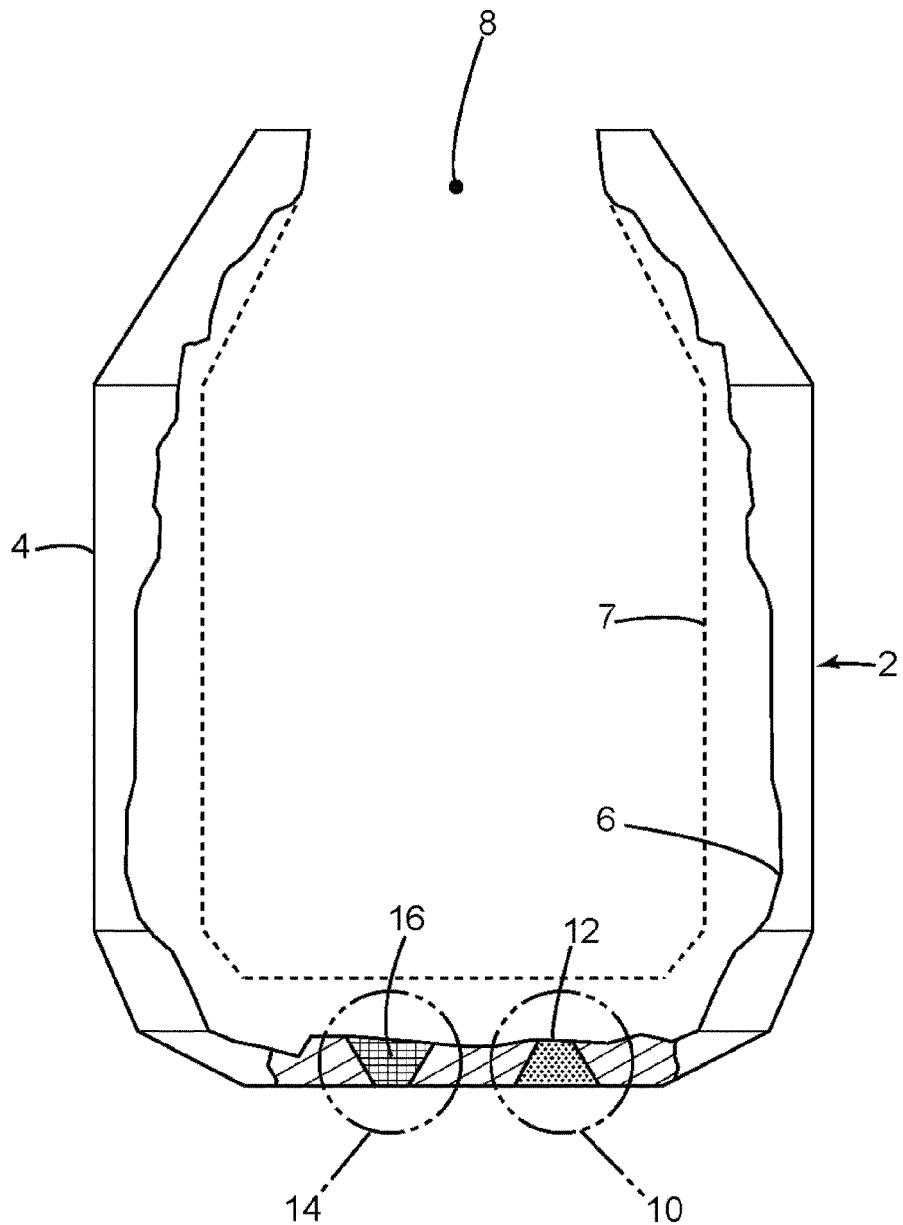
FIG. 1 illustrates a container configured to hold materials at elevated temperatures.

FIG. 1 illustrates a container 2 configured to hold materials at elevated temperatures. As used herein throughout, the term "container" or "vessel" is used interchangeably and broadly, including reference to all types of metallic or non-metallic vessels or containers of various sizes and shapes designed to hold materials at elevated temperatures that may be below, at or above the melting point of the vessel material. Examples of such containers or vessels are those used in applications such as, but not limited to, gasification processes in chemical and power production, Electric-Arc Furnaces (EAF), Basic Oxygen Furnaces (BOF), ladles, blast furnaces, degassers, and Argon-Oxygen-Decarburization (AOD) furnaces in steel manufacturing. In addition, as used herein throughout, the term materials at elevated temperature is used broadly to mean materials configured to be disposed inside these containers having temperatures high enough to cause damage to the container once the same is exposed thereto when the integrity of the refractory materials covering at least a portion of a surface of the container is somehow compromised so as to expose the container to the materials at the elevated temperatures. As shown, the container 2 has a shell 4, an internal layer of refractory material 6, and an opening 8. The dashed line 7 in FIG. 1 illustrates the original layer of refractory material 6 before the container was placed in use. In order to better explain the subject matter being disclosed, the container 2 has been illustrated with two areas in which local wear and tear from use has damaged the refractory material 6, as further explained below.

A first area 10 illustrates a location where a hole having a small opening 12 has developed in the refractory material 6. As understood by those skilled in the applicable arts, the first area 10 may also be illustrative of an area in the refractory material 6 where fining has developed, i.e., an area where, when in use, molten steel naturally enters small gaps (e.g., small openings with a characteristic dimension of approximately, for example, 1-5 mm) that develop between the bricks in a refractory-lined vessel. A second area 14 is also illustrated in FIG. 1 in which a piece of the refractory material 6 has been removed by use and slag buildup 16 on the interior of the container 2 has filled the void left by the refractory material that has been removed. One of the advantageous features of the subject matter disclosed is an improved ability to better identify areas 10 and 14 by a combination of lining thickness and external surface temperature measurements, as it will be further explained below. It should be understood that the areas 10 and 14 have been shown as examples of problems that may developed during use of the container 2 and in no way limit the scope of the subject matter being disclosed. That is to say, those of ordinary skill in the applicable arts will understand that there may be other types of defects that may be detected by the disclosed subject matter, as such, the mentioning of the exemplary areas 10 and 14 should in no way limit the scope of the disclosed subject matter.

Figure 2:
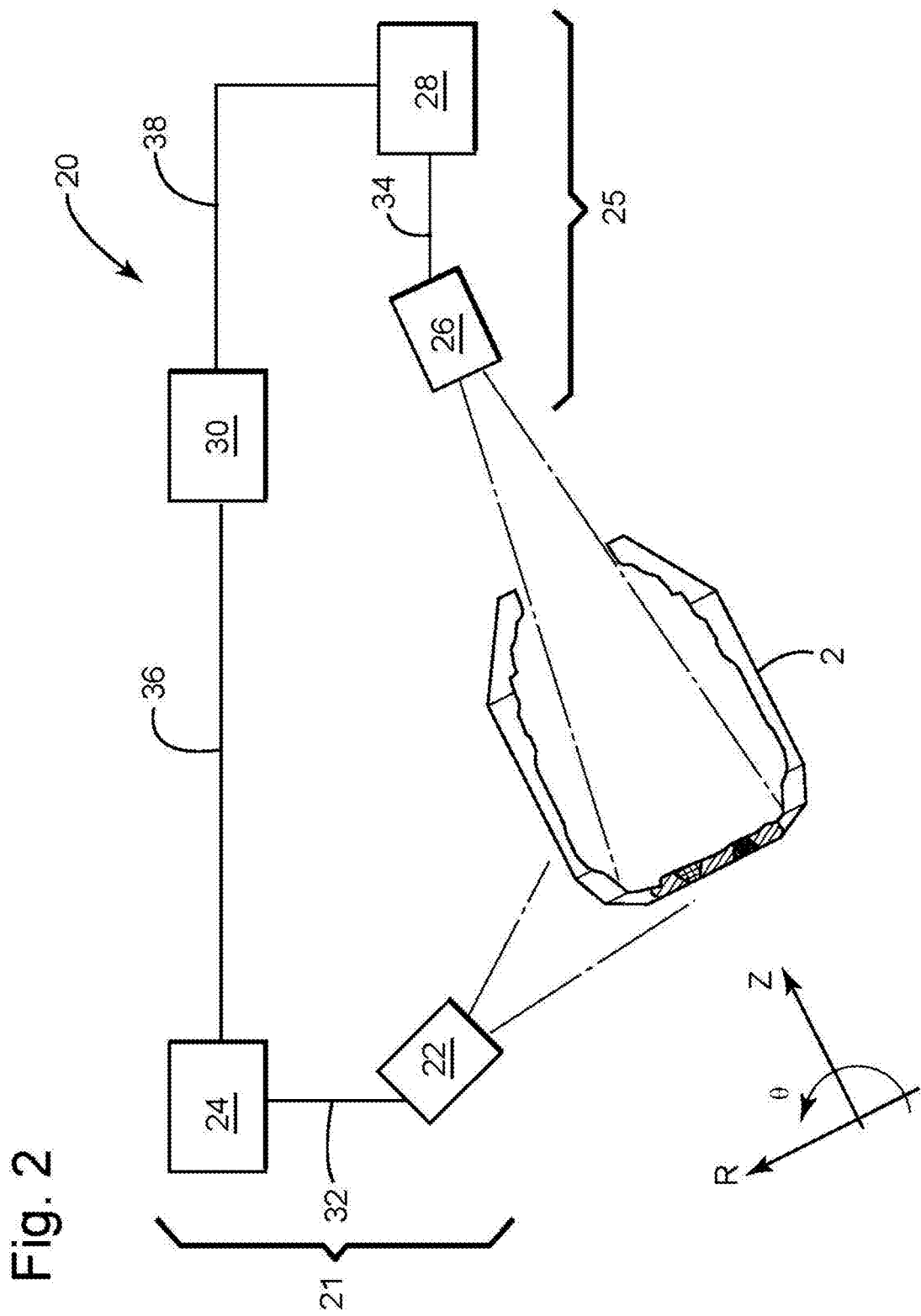
FIG. 2 illustrates a schematic diagram of an apparatus or system configured to monitor the integrity of the container of FIG. 1 according to an exemplary embodiment of the subject matter disclosed.

FIG. 2 illustrates a schematic diagram of an apparatus (or system) 20 configured to monitor the integrity of the container 2 of FIG. 1 according to an exemplary embodiment of the subject matter disclosed. As shown, the apparatus 20 includes a thermographic system or apparatus 21 to monitor the external surface temperature of the container 2 and a refractory thickness measuring system or apparatus 25 configured to monitor the thickness of the refractory material 6 inside the container 2. The thermographic system 21 includes a first radiation detector 22 and a first controller 24 associated therewith. The refractory thickness measuring system 25 includes a first radiation source 26 and a second controller 28 associated therewith. As also shown in the exemplary embodiment of FIG. 2, both the thermographic system 21 and the refractory thickness measuring system 25 are in communication with a central controller 30. In FIG. 2, the first radiation detector 22 is shown connected to the first controller 24 by use of a cable 32. Similarly, the first radiation source 26 is shown connected to the second controller 28 by a cable 34; and the first and second controllers 24 and 28 are shown connected to the central controller 30 by cables 36 and 38, respectively. However, those of ordinary skill will understand that these connections may be wireless in other embodiments and the controllers 24 and 26 may be individually provided as illustrated or combined into a single device with the central controller 30 or housed therein. That is; the interconnection and/or disposition of the devices illustrated in FIG. 2 do not limit the scope of the subject matter being disclosed, but is provides as an illustration of embodiments thereof. In addition, the number of radiation sources and detectors is not limited to a single one of each. For example, in one embodiment, the first radiation detector 22 includes a plurality of infrared (IR) detectors (or cameras) configured to measure the external surface temperature of the container 2 by radiative heat transfer from the container 2 to the external detectors 22 and the first radiation source 26 is a light source used to scan the interior of the container 2 so as to allow for the measurement of the thickness of the refractory material therein. In another embodiment, the first radiation source 26 is a range or distance scanner configured to measure the distance from the location of the system 25 to interior points on the surface of the refractory material 6. In yet another embodiment, the first radiation source 26 may be one having a selected wavelength spectrum, said spectrum possibly being visible or invisible to the naked eye. In other exemplary embodiments, the communications between the noted controllers and/or other components may take place via Internet, radio waves, microwaves, satellite or other known means in the art and the connections between the controllers may be wired or wireless.

In one embodiment the first radiation detector or detectors 22 may be installed in the mill where the container 2 is located, around the ladle, to yield a composite image of the entire ladle system. In another embodiment the first controller 24 may be a personal computer (PC) that reads the output of IR cameras and assembles a composite image from individual images together if multiple cameras are used. The thermographic data collected by the IR cameras may be acquired while the ladle or container 2 is hanging from a crane. Thus, in such embodiments, the relative orientation of the IR camera(s) and the ladle may be nominally constant from measurement to measurement. Post processing the composite image of the thermographic data in such embodiments may yield a spatially-resolved temperature profile in cylindrical coordinates, the independent coordinate variables being Z (distance from the ladle lip) and theta (the azimuthal position around the ladle circumference). R (the radial distance from the ladle centerline) may be redundant since the IR data is obtained only from the outer surface of the container. In some embodiments the operation of the systems 21 and 25 takes place concurrently, i.e., measurements of the external surface temperatures and internal liner thickness are made substantially simultaneously during the same stoppage of the vessel operation and combined and displayed to the user for assessment of the container 2. In other embodiments, the systems 21 and 25 are operated separately or sequentially during different stoppage of the vessel operation and their individual data later combined.

According to an exemplary embodiment, a typical configuration that could be used to measure the lining thickness in a ladle used in the steel industry is with the ladle placed in an appropriate stand (in this case the stand may be configured to rotate through a given angular displacement, e.g., 360°) at a given distance (e.g., approximately 3-5 m) in front of the laser scanner with measurements taken with the ladle mouth tilted towards the scanner. In another embodiment, range points to the interior of the ladle are measured as described in U.S. Pat. No. 6,922,252 (hereinafter the '252 patent which is assigned to the assignee of this document), the contents of which are incorporated herein by reference in their entirety.

In another embodiment, the laser system 25 may be installed in a fixed-position stand that is either kinematic or instrumented to determine the position of the ladle relative to the laser head. As understood by those of ordinary skill, in a kinematic embodiment, the ladle stand is constructed in such a way so as to position the ladle in the same position each time the same is placed in the stand. In an instrumented embodiment, single point laser range finders are used to measure the position of the ladle in the stand. In such embodiments, the spatial orientation of the laser data should be known to the uncertainty of the measurement, typically ±5 mm. The laser data may be also given in cylindrical coordinates, with R representing the local lining thickness at any given point in the ladle, as later illustrated. With both the laser and IR scanner data in the same coordinate representation, the central controller 30 combines an image representing the external surface temperature of the container 2 (e.g., using a false-colored composite image of the IR scanner in one embodiment) with a numerical representation of the local lining thickness at an appropriate grid density so as to preserve the clarity of the numerical thickness data. As further explained below, several algorithms are contemplated to produce such a combination of internal and external measurements in an efficient manner so as to allow the user to quickly and accurately determine where inconsistencies in the thickness and temperature measurements exist so as to allow an improved capability to detect potential container failures. One of the advantageous features of the subject matter disclosed herein is the fact that the qualitative IR scanner information and the quantitative lining thickness data eliminate, or substantially reduce the limitations of each measurement operating independently. General lining thinning and wear rate analysis can be completed with the lining thickness data from the laser scanner. Finning is easily observable in areas where the lining thickness remains acceptably high, but high external ladle shell temperatures are noted. Confirmation of thin linings, independent of slag build up, are observable in regions where the laser scanner suggests reduced lining thickness and the IR scanner shows elevated surface temperature.

Thus, one of the advantageous features of the subject matter disclosed is the combination of lining thickness data obtained from a laser scanning of the ladle interior with IR thermographic measurements of the exterior surface of the ladle shell. Those of ordinary skill will understand that correlating internal refractory thickness with the external temperature will aid in verifying the internal thickness measurements. When combined as proposed herein the measurements will complement one another, i.e., the limitations of one compensated by the capabilities of the other. A laser scanner difficulty in detecting potential failures due to finning may be complemented with a thermographic scanner capable of detecting incipient rise in shell temperature. Conversely, the IR scanner systems' lack of quantitative information describing the lining thickness is produced in the data of the laser scanner. However, by combining the data from both systems, a comprehensive ladle analysis tool is created that provides breakout protection, as well as quantitative information characterizing wear rates and local lining thickness. Such systems can be operated simultaneously or sequentially. In addition, inconsistencies in the data, e.g. areas that show high temperature and high lining thickness, may be quickly and efficiently detected and inspected further for molten metal creep or small holes in the lining—all of which can contribute to lining failure. As such, the subject matter disclosed enhances operational safety. Moreover, enhanced detection of impending ladle failure leads to significant cost savings by avoiding loss of value added product, costly cleanup operations, and potential production down time. In addition, the automated nature of the implementation allows the system to acquire and present data to the user quickly, through a simplified interface.

Moreover, the combined presentation yields an immediate correlation between hot spots and local reduction in lining thickness. Areas showing thicker lining, but high shell temperatures can immediately be investigated for either slag accumulation or finning, or small holes/missing bricks in the ladle that were not detected by the laser scan. Areas that show low temperature but thin lining are likely not affected by finning, but must be addressed on the basis of limited remaining lining life alone.

Figure 3:
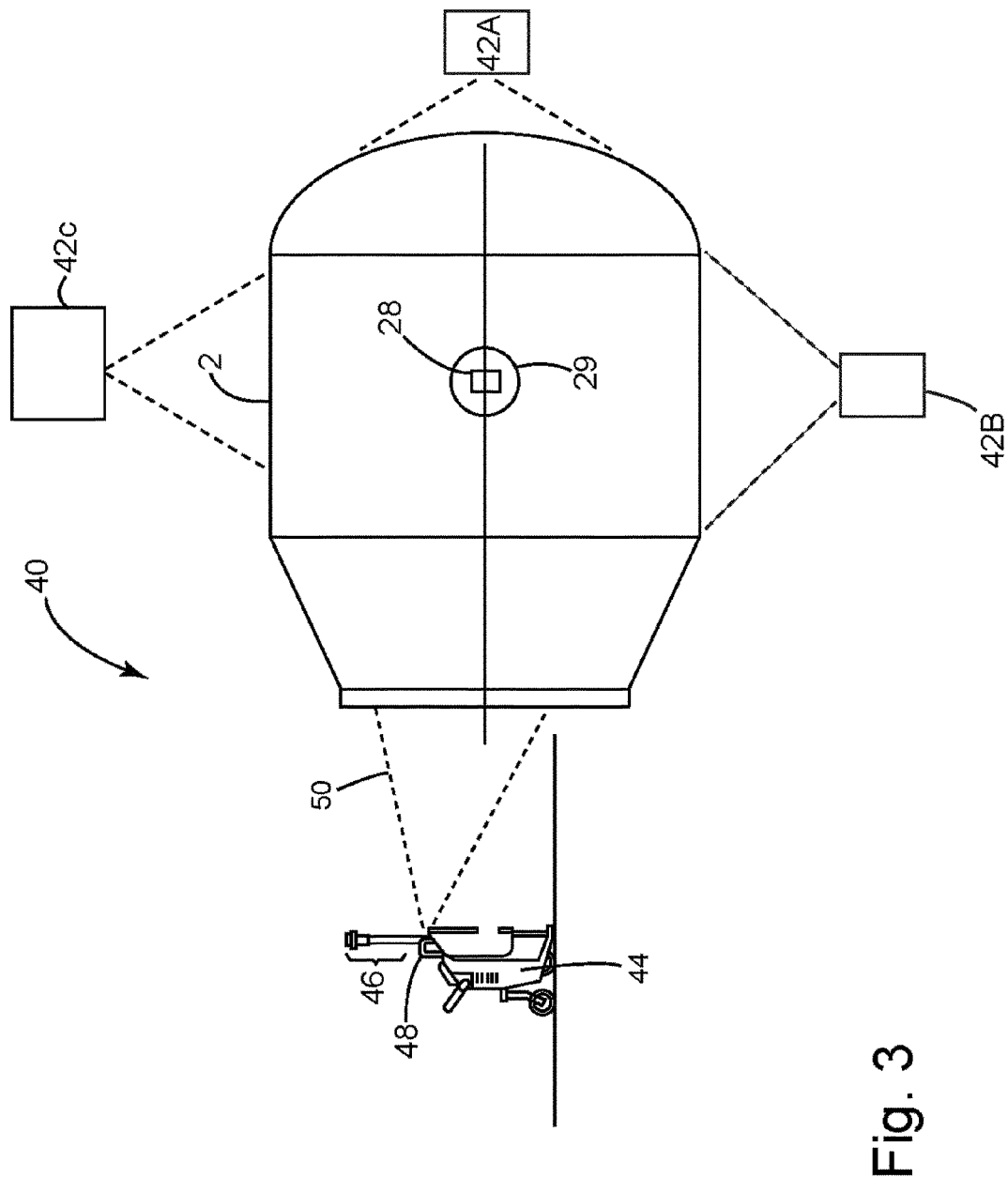
FIG. 3 illustrates a schematic diagram of an apparatus or system configured to monitor the integrity of the container of FIG. 1 according to another exemplary embodiment of the subject matter disclosed.

FIG. 3 illustrates a schematic diagram of an apparatus 40 configured to monitor the integrity of the container 2 of FIG. 1 according to another exemplary embodiment of the subject matter disclosed. In this exemplary embodiment, five IR cameras 42A-42E (cameras 42D and 42E are not shown for simplicity). Four of the cameras (42B-42E) are used to monitor the external surface of the container 2 on four quadrants of the lateral mall of the container and another camera (42A) monitors the bottom of the container. The refractory lining thickness measurement are made in this embodiment by use of a mobile cart 44 that includes a tracking system 46 and a contouring system 48 mounted thereon as disclosed in the '252 patent. However, it should be noted that the subject matter disclosed herein should not be limited in any way by the use of the mobile cart 44 and/or the five IR cameras 42A-42E. Different configurations of the invention are possible that will take into account space availability and particular requirements of a given application. For example, fixed position laser measurement devices may also be used for ladle measurement. These devices may be positioned above a transfer car, or adjacent a slide gate maintenance station in other embodiments. Arrangements of the present invention, such as reference marks configured to aid in the positioning of the mobile cart 44 (not shown in FIG. 3) may be anchored to the floor, building columns, or in the hood area are also possible. In either mobile or fixed-position embodiments, the laser may be placed as close to the vessel mouth as possible so as to maximize the field of view.

As understood by those of ordinary skill in the art, embodiments that use a mobile scanner may simplify the process of acquiring refractory thickness date by eliminating the need to use fixing points at or near the high-temperature container. In addition, if the measurement system is mobile and the terrain over which it moves is irregular, an accurate determination of the position of the measurement system relative to the container is required. However, as understood by those of ordinary skill, placement of sensors is dependent on the nature of the application and the degrees of freedom in the installation of the container and should not limit the scope of the subject matter for which patent protection is sought. For example, in embodiments configured to characterize a BOF, the only unknown degree of freedom may be the tilt of the furnace. In ladle applications that use fixed-position instrumentation, the disclosed measurements may be automated. In ladle applications, the vessel may typically be brought to the disclosed measuring system, whereas in BOF/converter applications the disclosed measuring system may be brought to the vessel. For applications involving ladles, one of the advantageous features of a particular embodiment may be a single-button operation, i.e., with the ladle in the measurement position, an operator may need only to press a "measure" button, and the system will automatically scan the ladle and report results. In other embodiments, single-button operation may be implemented for the IR scanner, though control may be typically initiated from a crane cab.

In the illustrated embodiment, one of the components of the contouring system 48 is a sensor that measures range, i.e., the distance from the contouring system to a target, and location of that target with respect to the range sensor. In operation, optical radiation 50 from an optical radiation source in the contouring system 48 is emitted to the inside of the container and the reflected optical radiation from the inside of the container is detected back by the contouring system. Based on the time taken between the emitted and reflected radiation to leave and reach the contouring system, respectively, and the characteristics of the radiation source, the distance between the contouring system and the surface of the container that cause the radiation reflection can be measured. Typical range measurement systems use a scanned beam to quickly record multiple positions and ranges.

Figure 4:
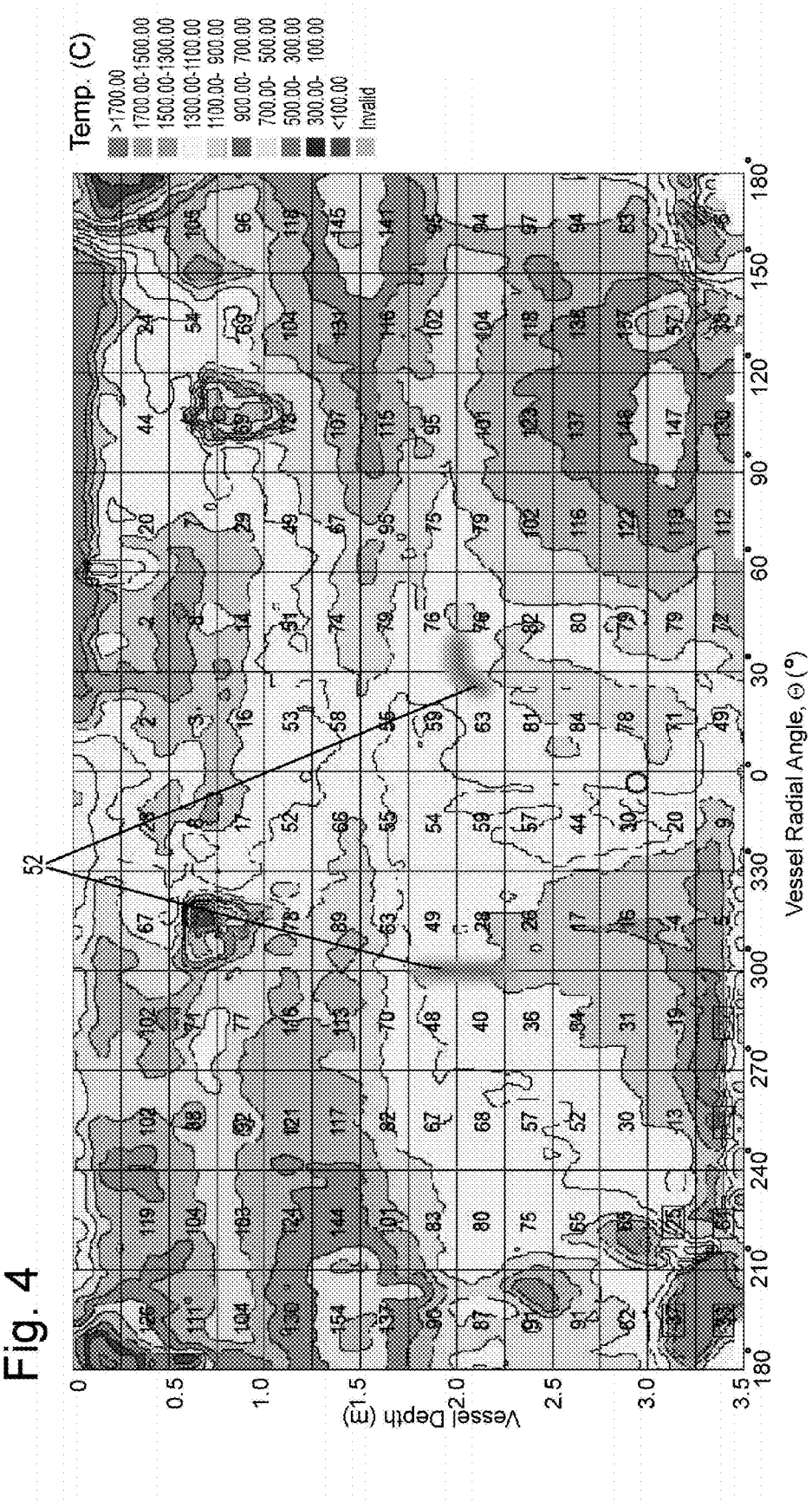
FIG. 4 illustrates a simulated lining thickness profile and a simulated external surface temperature profile according to an exemplary embodiment.
Figure 5:
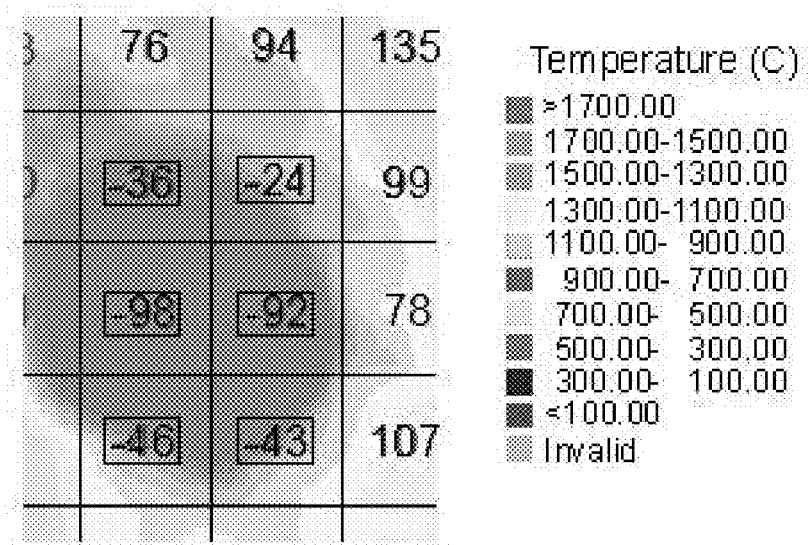
FIG. 5 illustrates an exemplary portion of a simulated lining thickness profile and a simulated external surface temperature profile according to an exemplary embodiment.

Exemplary measurements using embodiments of the disclosed subject matter are illustrated in FIGS. 4 and 5. As understood by those of ordinary skill in the applicable arts, the subject matter disclosed herein is not in any way limited by the exemplary temperature scales represented in FIGS. 4 and 5. FIG. 4 illustrates a refractory thickness profile represented by spatially resolved quantitative values corresponding to local thickness of the refractory material both as a function of vessel depth and angular position. Thickness, reported in either mm or inches, is reported relative to a defined surface in the vessel. This defined surface can be the inner or outer metallic shell of the vessel, the inner surface of the safety lining (the backup refractory brick that normally remains permanently installed in the vessel), or the inner surface of the working lining (the primary refractory brick that is replaced during a normal vessel reline). Surface temperature measurements are also illustrated in FIG. 4 by use of contour lines defining areas having different gray-scale colors representing different temperature levels as shown in the legend of that figures. FIG. 5 illustrates similar results but for a smaller portion of the container.

As shown in FIG. 4, there are at least two regions (labeled 52 in FIG. 4) in which the external temperature has reached high values; however, the refractory thicknesses of the working lining in those regions are on average 49 mm or so on the region 52 located on the left and around 76 mm for the region 52 located to right. For this vessel, the starting thickness values of the working lining were 110 mm and the ladle will be removed from service when the lining thickness reaches 10 mm. As previously explained, the two regions 52 in FIG. 4 are exemplary regions where fining has most likely taken place (e.g., area 10 illustrated in FIG. 1) and the refractory thickness measurements have not detected this problem. That is, the molten steel from a previous melting cycle has naturally entered small gaps (e.g., small openings relative to the diameter of the radiation source) between the container bricks undetected by the refractory scanning system. As such, using only the scanning system to detect such a problem would take longer until the finning develops further such that the scanning system would detect those openings in the refractory material, or the probability may be high that the scanning system may not detect the finning. The results of FIG. 5 illustrated measurements in a region of the container where the external surface temperature is high and the refractory thickness thin, suggesting that a hole in the lining of the vessel exists in that particular location (e.g., area 14 illustrated in FIG. 1).

Figure 6:
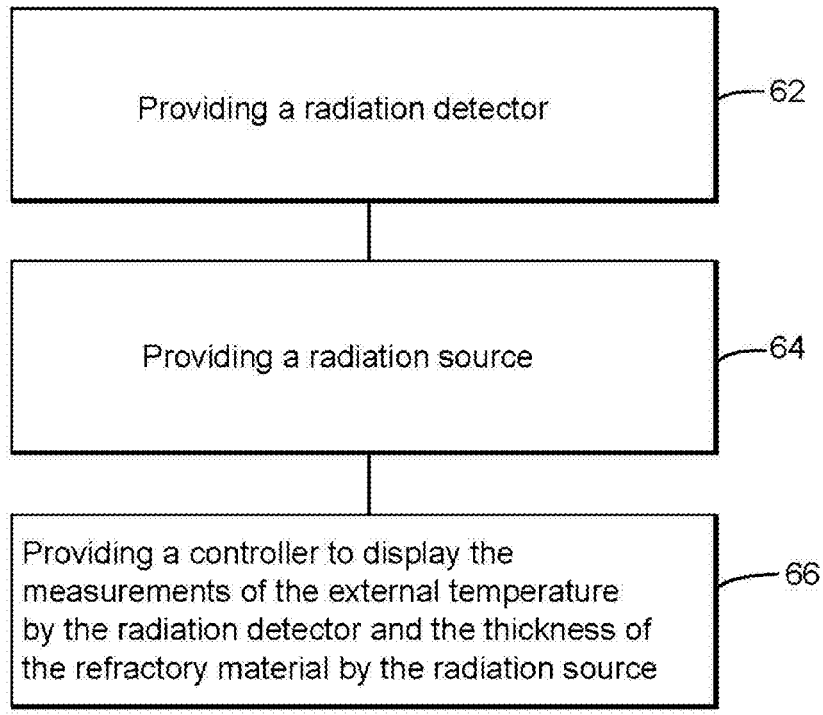
FIG. 6 illustrates a flowchart of a method for monitoring the integrity of a container having a protective refractory layer.

According to another exemplary embodiment, a process or method for monitoring the integrity of a container having an internal layer of a refractory material is disclosed as illustrated in the flowchart shown in FIG. 6. As this process is intended to be as complete as possible, it is noted that not all the steps need to be performed for monitoring the integrity of the container. In other words, some steps to be described next may be optional.

As shown in FIG. 6, the method for monitoring the integrity of a container having an internal layer of a refractory material includes the steps of providing a first radiation detector configured to measure an external surface temperature of the container at 62; providing a first radiation source configured to measure a thickness of the refractory material at 64; and, at 66, providing a central controller configured to display to a user the measurement of the external surface temperature of the container and the measurement of the thickness of the refractory material.

Figure 7:
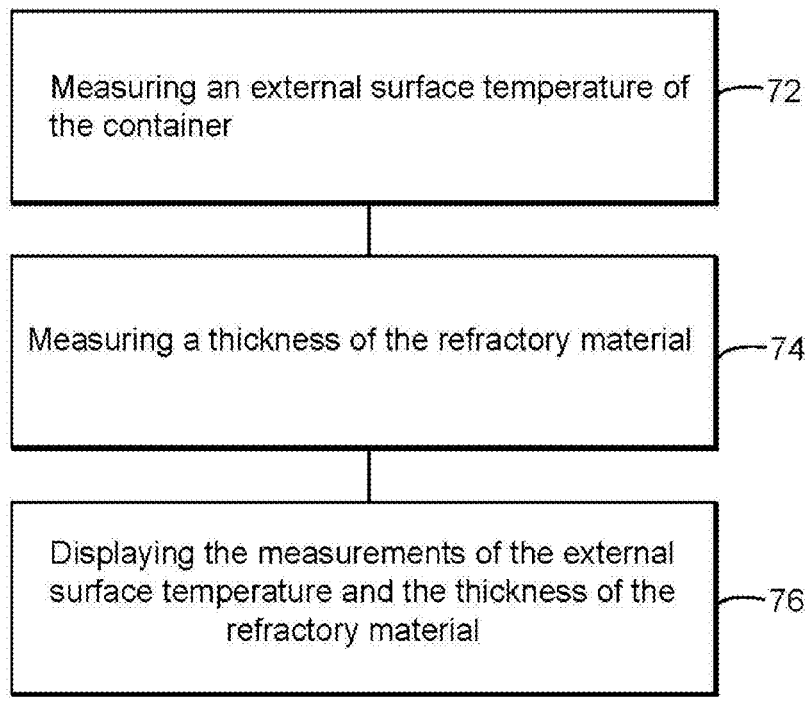
FIG. 7 illustrates a flowchart of a method for monitoring the integrity of a container having a protective refractory layer.

According to another exemplary embodiment, a process or method for monitoring the integrity of a container having an internal layer of a refractory material is disclosed as illustrated in the flowchart shown in FIG. 7. As this process is intended to be as complete as possible, it is noted that not all the steps need to be performed for monitoring the integrity of the container. In other words, some steps to be described next may be optional. As shown in FIG. 7, the method for monitoring the integrity of a metallic container having an internal layer of a refractory material includes the steps of measuring an external surface temperature of the container with a first radiation detector at 72; measuring a thickness of the refractory material with a first radiation source at 74; and, at 76, displaying to a user the measurement of the external surface temperature of the container and the Measurement of the thickness of the refractory material.

Figure 8:
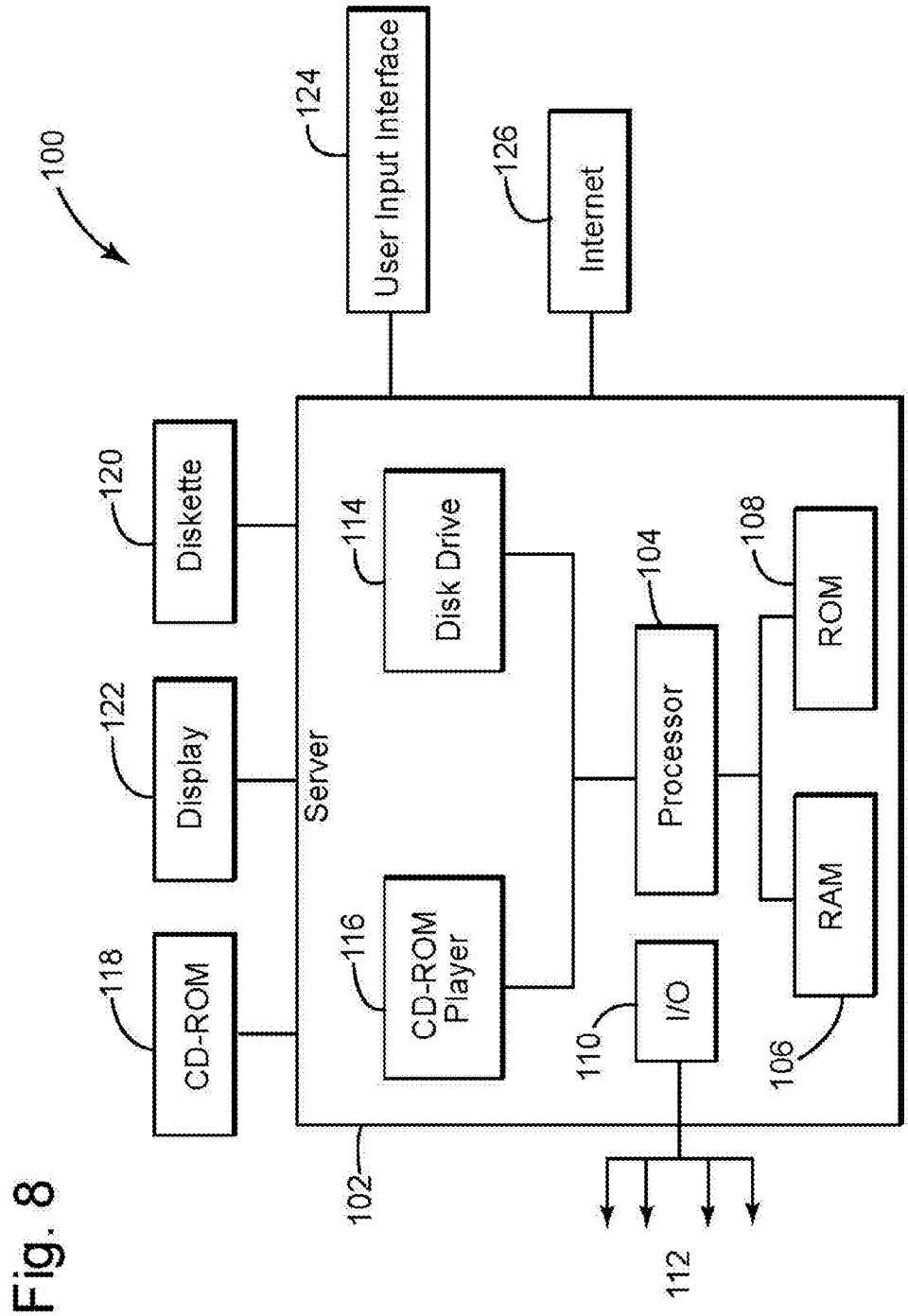
FIG. 8 is a schematic diagram of a control device of a system or apparatus configured to identify potential failures locations in a vessel adapted to hold materials at elevated temperatures according to an exemplary embodiment.

Finally, an example of a representative control device or controller 100 capable of carrying out operations in accordance with the exemplary embodiments discussed above is illustrated in FIG. 8. Hardware, firmware, software or a combination thereof may be used to perform the various steps and operations described herein. In various examples of the subject matter disclosed, the central controller 30, the first controller 24, and/or the second controller 28 of FIG. 2 individually or in any combination are part of a system containing the control device or controller 100 in the form of a computing structure that may be used in connection with such a system.

The exemplary central controller 100 suitable for performing the activities described in the exemplary embodiments may include a server 102, which may correspond to any of controllers 24, 28, and/or 30 in FIG. 2. Such a server 102 may include a central processor (CPU) 104 coupled to a random access memory (RAM) 106 and to a read-only memory (ROM) 108. The ROM 108 may also be other types of storage media to store programs, such as programmable ROM (PROM), erasable PROM (EPROM), etc. The processor 104 may communicate with other internal and external components through input/output (I/O) circuitry 110 and bussing 112 to provide control signals and the like. The processor 104 carries out a variety of functions as is known in the art, as dictated by software and/or firmware instructions.

The server 102 may also include one or more data storage devices, including, for example, hard and floppy disk drives 114, CD-ROM drives 116, and/or other hardware capable of reading and/or storing information such as DVD, etc. In one embodiment, software for carrying out the above discussed steps may be stored and distributed on a CD-ROM 118, diskette 120 or other form of media capable of portably storing information. These storage media may be inserted into, and read by, devices such as the CD-ROM drive 116, the disk drive 114, etc. The server 102 may be coupled to a display 122, which may be any type of known display or presentation screen, such as LCD displays, plasma display, cathode ray tubes (CRT), etc. A user input interface 124 may be provided, including one or more user interface mechanisms such as a mouse, keyboard, microphone, touch pad, touch screen, voice-recognition system, etc.

The server 102 may be coupled to other computing devices, such as landline and/or wireless terminals and associated applications, via a network. The server may be part of a larger network configuration as in a global area network (GAN) such as the Internet 126, which allows ultimate connection to the various landline and/or mobile client devices.

In the detailed description of the exemplary embodiments, numerous specific details are set forth in order to provide a comprehensive understanding of the claimed invention. However, one skilled in the art would understand that various embodiments may be practiced without such specific details.

As also will be appreciated by one skilled in the art, the exemplary embodiments may be embodied in a wireless communication device, a telecommunication network, as a method or in a computer program product. Accordingly, the exemplary embodiments may take the form of an entirely hardware embodiment or an embodiment combining hardware and software aspects. Further, the exemplary embodiments may take the form of a computer program product stored on a computer-readable storage medium having computer-readable instructions embodied in the medium. Any suitable computer readable medium may be utilized including hard disks, CD-ROMs, digital versatile disc (DVD), optical storage devices, or magnetic storage devices such a floppy disk or magnetic tape. Other non-limiting examples of computer readable media include flash-type memories or other known types of memories.

The disclosed exemplary embodiments provide an apparatus, a system and a method for identifying potential failure locations in a metallic container configured to hold materials at elevated temperatures. It should be understood that this description is not intended to limit the invention. On the contrary, the exemplary embodiments are intended to cover alternatives, modifications and equivalents, which are included in the spirit and scope of the invention as defined by the appended claims.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. An apparatus configured to monitor the integrity of a container protected by a refractory material, the apparatus comprising:
   A thermographic system having a first radiation detector, said thermographic system being configured to make spatially resolved temperature measurements of an external surface of the container;
   a scanning system having a first radiation source, a scanner, optics, a photodetector, and receiver electronics, said scanning system being configured to make spatially resolved thickness measurements of the refractory material; and
   a central controller configured to display to a user the spatially resolved temperature measurements of the external surface of the container and the spatially resolved thickness measurements of the refractory material, wherein a defect on the refractory material is identified by a combination of the spatially resolved temperature measurements of the external surface of the container and the spatially resolved thickness measurements of the refractory material.

2. The apparatus according to claim 1, wherein the thermographic system comprises a first controller, said first controller being configured to communicate with said central controller.

3. The apparatus according to claim 1, wherein the thermographic system first radiation detector is a plurality of thermographic systems each comprising a first controller, each of said first controllers being configured to communicate with said central controller.

4. The apparatus according to claim 1, wherein the spatially resolved temperature measurements of the external surface of the container and the spatially resolved thickness measurements of the refractory material are made substantially simultaneously.

5. The apparatus according to claim 1, wherein the scanning system comprises a first controller and the scanning system and the first controller are disposed in a fixed-position stand, the first controller being in communication with the central controller.

6. The apparatus according to claim 1, wherein the scanning system comprises a first controller and the scanning system and the first controller are disposed in a mobile unit, the first controller being in communication with the central controller.

7. The apparatus according to claim 1, wherein a fining in a location inside the container is detected by a localized temperature measurement of the external surface of the container being above a threshold temperature value and by a corresponding localized thickness measurement of the refractory material being above a minimum thickness threshold value.

8. The apparatus according to claim 1, wherein a molten metal creep or a small hole in the refractory material in a location inside the container is detected by a localized temperature measurement of the external surface of the container being above a threshold temperature value and by a corresponding localized thickness measurement of the refractory material being above a minimum thickness threshold value.

9. The apparatus according to claim 1, wherein the scanning system is disposed in a mobile cart and further comprises a tracking system and a contouring system mounted thereon.

10. The apparatus according to claim 1, wherein the scanning system further comprises a contouring system configured to measure range data from the contouring system to an internal surface of the refractory material.

11. The apparatus according to claim 1, wherein the container is configured to be used in a gasification process in chemical and/or power production, in an electric-arc furnace, in a basic oxygen furnace, in a ladle, in a blast furnace, in a degasser, or in an argon-oxygen-decarburization furnace.

12. The apparatus according to claim 1, wherein the thermographic system comprises a first controller, the scanning system comprises a second controller, and the first controller, the second controller, and the central controller are in communication with each other.

13. The apparatus according to claim 12, wherein the first controller, the second controller, and the central controller are disposed in a single controlling unit.

14. The apparatus according to claim 1, wherein a monitoring of the container is configured to be performed with the container placed kinematically on a stand with the container placed substantially in a given position before making the spatially resolved thickness measurements or by determining the position of the container on the stand before making the spatially resolved thickness measurements.

15. A method for monitoring the integrity of a container having an internal layer of a refractory material, the method comprising:
   taking spatially resolved temperature measurements of an external surface of the container with a thermographic system;
   taking spatially resolved thickness measurements of the refractory material with a scanning system; and
   detecting a defect on the refractory material by a combination of the spatially resolved temperature measurements of the external surface of the container and the spatially resolved thickness measurements of the refractory material.

16. The method according to claim 15, wherein the detecting further comprises detecting a fining in a location inside the container by identifying a localized temperature measurement of the external surface of the container above a threshold temperature value and a corresponding localized thickness measurement of the refractory material above a minimum thickness threshold value.

17. The method according to claim 15, wherein the detecting further comprises detecting a molten metal creep or a small hole in the refractory material in a location inside the container by identifying a localized temperature measurement of the external surface of the container above a threshold temperature value and a corresponding localized thickness measurement of the refractory material above a minimum thickness threshold value.

18. The method according to claim 15, wherein the taking of spatially resolved thickness measurements of the refractory material further comprises:
   positioning the container on a stand; and
   taking the thickness measurements with the container maintained substantially in a given position; or
   determining the position of the container on the stand before taking the thickness measurements.

19. The method according to claim 15, wherein the scanning system comprises a first controller and the scanning system and the first controller are disposed in a fixed-position stand.

20. The method according to claim 15, wherein the scanning system comprises a first controller and the scanning system and the first controller are disposed in a mobile unit.

* * * * *